United States Patent
Begovich et al.

(10) Patent No.: US 10,253,349 B2
(45) Date of Patent: Apr. 9, 2019

(54) MULTIPLEX PCR TO DETECT GENE FUSIONS

(71) Applicant: Roche Molecular Systems, Inc., Pleasanton, CA (US)

(72) Inventors: Ann Begovich, El Cerrito, CA (US); Rajiv Dua, Manteca, CA (US); Dwight Kuo, Castro Valley, CA (US); Xiaoju Max Ma, San Carlos, CA (US); Ellen Ordinario, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 350 days.

(21) Appl. No.: 15/130,486

(22) Filed: Apr. 15, 2016

(65) Prior Publication Data

US 2016/0304937 A1    Oct. 20, 2016

Related U.S. Application Data

(60) Provisional application No. 62/149,381, filed on Apr. 17, 2015.

(51) Int. Cl.
*C12Q 1/68* (2018.01)
*C12Q 1/6806* (2018.01)
*C12Q 1/6809* (2018.01)
*C12Q 1/6858* (2018.01)
*C12Q 1/686* (2018.01)

(52) U.S. Cl.
CPC .......... *C12Q 1/6806* (2013.01); *C12Q 1/686* (2013.01); *C12Q 1/6809* (2013.01); *C12Q 1/6858* (2013.01)

(58) Field of Classification Search
None
See application file for complete search history.

(56) References Cited

U.S. PATENT DOCUMENTS

2004/0023207 A1* 2/2004 Polansky ............... A61K 31/00 435/5

FOREIGN PATENT DOCUMENTS

WO    2004024916    3/2004

OTHER PUBLICATIONS

Soda et al. Identification of the transforming EML4-ALK fusion gene in non-small-cell lung cancer. Nature 448:561-566. (Year: 2007).*
Gruber (2014) J. Thoracic. Oncol. 9:307.
Gerrard (2011) Am. J. Hematol. 86:313.
Jieping (2014) PLoS One 9 e110641.
Maruja (2014) J. Mol. Diagn. 16:229.

* cited by examiner

*Primary Examiner* — Samuel C Woolwine
(74) *Attorney, Agent, or Firm* — Carol Johns

(57) ABSTRACT

Provided herein are methods and compositions for detecting gene fusions, e.g., relevant to cancer. The present methods and compositions can be used to detect gene fusions with very high sensitivity and specificity. The present methods and compositions can detect gene fusions, e.g., in free circulating tumor RNA from a plasma sample.

7 Claims, 4 Drawing Sheets

Specification includes a Sequence Listing.

MULTIPLEX PCR TO DETECT GENE FUSIONS

CROSS-REFERENCE TO RELATED APPLICATIONS

The present application claims priority to U.S. Provisional Application No. 62/149,381 filed Apr. 17, 2015, the disclosure of which is incorporated by reference herein in its entirety.

SEQUENCE LISTING

The instant application contains a Sequence Listing which has been submitted electronically in ASCII format and is hereby incorporated by reference in its entirety. Said copy, created on Apr. 8, 2016, is named 32841-US-1 SL.txt and is 46,097 bytes in size.

BACKGROUND OF THE INVENTION

A number of cancers are associated with gene fusions. Perhaps the earliest reported example is the association of BCR-ABL with chronic myelogenous leukemia (CML) in the '60s (Nowell and Hungerford (1960) *J. Natl. Cancer Inst.* 25:85). Since then, hundreds more gene fusions have been reported for cancers in many different tissues (Presner and Chinnaiyan (2009) *Curr. Opin Genet. Dev.* 19:82).

Another example is the tyrosine receptor kinase ALK, EML4-ALK (echinoderm microtubule-associated protein like 4-anaplastic lymphoma kinase) fusions are associated with non-small cell lung cancer (NSCLC). In this case, the N terminal, extracellular portion of ALK is replaced by EML4 (KIF5B, HIP1, KLC1, TFG can also fuse with ALK in a similar manner). The expression of the resulting fusion gene is driven by the strong EML4 promoter, resulting in higher expression of the intracellular tyrosine kinase domain of ALK. In addition, EML4 forms a coiled-coil that results in ligand-independent dimerization, and constitutive activation of the ALK tyrosine kinase domain.

Detection of a gene fusion is important for directing therapy. Most current methods of detection require biopsy of tumor tissue, which is not feasible for many cancer patients, especially in later stages. Detection in biopsied tissue sections is typically carried out by fluorescence in situ hybridization (FISH) or immunohistochemistry (IHC). The tests have high false positive rates and background, in part because of shearing during the sectioning process. Skilled cytologists are thus required to observe multiple tissue sections, which necessitates a sizable biopsy from a weakened patient. Detection of fusions has also been attempted using RT-PCR, but this has not been successful because of the highly variable nature of gene fusions. In the case of EML4-ALK4, at least 20 different fusions result in the activated tyrosine kinase. Another difficulty with RT-PCR is the amount and quality of genetic material from tumor tissue, e.g., in formalin fixed paraffin embedded (FFPE) form. See, e.g., Liu et al. (2015) PLoSOne 10: e0117032.

Because detection is time and resource intensive, the testing rate is relatively low. Cancers associated with ALK fusions are very sensitive to ALK inhibitors such as crizotinib and ceretinib. Gene fusions with Rearranged during Transcription (RET), such as with KIF5B or CCDC6, are also sensitive to therapy, e.g., with vandetanib (see Matsubara et al. (2007) *J. Thorac. Oncol.* 7:1872). The low rate of testing for gene fusions thus represents a great lost opportunity for treatment.

SUMMARY OF THE INVENTION

Provided herein are methods and compositions for detecting genetic fusions, e.g., fusion genes.

Provided is a composition comprising (1) at least one first primer pair that is specific for a fusion site between a first genetic region and a second genetic region, wherein the first and second genetic regions are not adjacent in a wild type genome, and wherein the st least one primer pair comprises at least one forward primer beginning on the 5' side of the fusion site and at least one reverse primer beginning on the 3' side of the fusion site; (2) a second primer pair specific for a portion of the first genetic region that is 5' of the fusion site; and (3) a third primer pair specific for a portion of the first genetic region that is 3' of the fusion site. Alternatively, the second and third primer pairs can be specific for the second genetic region.

In some embodiments, the first genetic region is in gene (e.g., gene 1). In some embodiments, the second genetic region is in a gene (e.g., gene 2). In some embodiments, the first and second genetic regions are in genes, where the fusion point between the genes in not found in a wild type genome. In some embodiments, the at least one first primer pair (1) comprises at least one forward primer that begins in gene 2, 5' of the fusion site, and optionally includes the fusion site. In some embodiments, the at least one first primer pair (1) comprises at least one reverse primer that begins in gene 1, 3' of the fusion site, and optionally includes the fusion site. In some embodiments, the at least one first primer pair comprises at least 2, 3, 4, 5, 6, 7, 8, 9, 10, or more primer pairs.

In some embodiments, the composition further comprises at least one primer pair specific for a control sequence, e.g., an internal control. Examples of controls that can be used for the presently disclosed assays include, but are not limited to SDH (succinate dehydrogenase), LDHA (lactate dehydrogenase A), NONO, PGK (phosphoglycerate kinase 1), PPIH, HPRT1, beta-actin, GADPH, ACTB, and 16S rRNA.

In some embodiments, each primer set ((1), (2), (3), and the optional at least one control primer pair) is associated with a different label (e.g., dye) that emits a signal distinct from the other labels. The label can be attached directly or indirectly to either the forward primer or reverse primer of each primer pair. In some embodiments, the labels are retained so that the amplification products resulting from each primer set ((1), (2), (3), and the optional at least one primer pair) are labeled. In some embodiments, the composition comprises at least one labeled probe specific for each of the amplification products resulting from each primer set ((1), (2), (3), and the optional at least one primer pair).

In some embodiments, the composition further comprises a DNA polymerase, e.g., a thermostable DNA polymerase such as Taq or a Taq derivative. In some embodiments, the composition further comprises reverse transcriptase. In some embodiments, the composition further comprises dNTPs. In some embodiments, the composition further comprises buffer amenable to polymerization by the DNA polymerase and reverse transcriptase.

In some embodiments, the composition further comprises a biological sample from an individual or group of individuals. In some embodiments, the individual has been diagnosed with cancer, e.g., lung cancer (e.g., non-small cell lung cancer (NSCLC), lung squamous cell carcinoma, lung adenocarcinoma), bladder carcinoma, glioblastoma, head and neck cancer, glioma, thyroid carcinoma, ovarian cancer, leukemia, lymphoma, prostate cancer, pancreatic cancer, renal cancer, or breast cancer.

In some embodiments, the sample is isolated nucleic acid, e.g., DNA or RNA. In some embodiments, the sample is RNA, e.g., isolated from blood (serum or plasma), bronchoalveolar lavage, or tissue biopsy. In some embodiments, the biological sample includes 100 nM or less of the polynucleotide comprising the fusion gene, e.g., 0.01-100 nM, 0.01-25 nM, 0.01-5 nM, 0.02-0.5 nM, or 0.02-0.1 nM.

In some embodiments, the first genetic region (gene 1) is selected from the group consisting of ALK, RET, ROS, NTRK, BRAF, ARL, and FGFR. In some embodiments, the first genetic region is ALK, and the second genetic region (gene 2) is selected from the group consisting of EML4, KIF5B, HIP1, KLC1, and TFG. In some embodiments, the first genetic region is RET, and the second genetic region (gene 2) is selected from the group consisting of KIF5B, CCDC6, NCOA4, and TRIM33.

In some embodiments, gene 1 is ALK and gene 2 is EML4. In some embodiments, the at least one first primer pair comprises at least one forward primer comprising a sequence selected from SEQ ID NOs:1-51, and at least one reverse primer comprising a sequence selected from SEQ ID NOs:52-62. In some embodiments, the second primer pair comprises a forward primer comprising a sequence selected from SEQ ID NOs:63-67 and a reverse primer comprising a sequence selected from SEQ ID NO:68-72. In some embodiments, the third primer pair comprises a forward primer comprising a sequence selected from SEQ ID NOs:73-77 and a reverse primer comprising a sequence selected from SEQ ID NOs:78-82.

In some embodiments, gene 1 is RET and gene 2 is CCDC6. In some embodiments, the first primer pair comprises at least one forward primer comprising a sequence selected from SEQ ID NOs:83-160, and at least one reverse primer comprising a sequence selected from SEQ ID NOs: 161-198. In some embodiments, the second primer pair comprises a forward primer comprising the sequence of SEQ ID NO:199 and a reverse primer comprising the sequence of SEQ ID NO:200. In some embodiments, the third primer pair comprises a forward primer comprising the sequence of SEQ ID NO:201 and a reverse primer comprising the sequence of SEQ ID NO:202.

Further provided are methods for defecting a genetic fusion in a biological sample, i.e., determining if the biological sample includes a polynucleotide with a genetic fusion or fusion gene (be it in DNA, or expressed RNA). In some embodiments, the method comprises (1) carrying out an amplification reaction with biological sample and the compositions as described herein and above; (2) determining the amount of amplification product from the at least one first primer pair (e.g., by detecting the signal from the label associated with the at least one first primer pair); (3) detecting the presence or absence of a difference in the amount of amplification product from the second primer pair and the amount of amplification product from the third primer pair (e.g., by detecting and comparing the signals of the labels associated with the second and third primer pairs); and (4) detecting a genetic fusion if (i) the amount of amplification product from the at least one first primer pair determined in step (2) is greater than the amount of amplification product from the at least one first primer pair and a control polynucleotide that does not carry the fusion gene; or (ii) the presence of a difference is detected in step (3).

In some embodiments, the method is carried out with biological sample and composition comprising (a) at least one first primer pair (e.g., at least 2, 3, 4, 5, 6, 7, 8, 9, 10 or more primer pairs) specific for a fusion site between a first genetic region (e.g., gene 1) and a second genetic region (e.g., gene 2), wherein the first and second genetic regions are not adjacent in a wild type genome, and wherein the at least one primer pair comprises at least one forward primer beginning on the 5' side of the fusion site and at least one reverse primer beginning on the 3' side of the fusion site; (b) a second primer pair specific for a portion of the first genetic region that is 5' of the fusion site; and (c) a third primer pair specific for a portion of the first genetic region that is 3' of the fusion site.

In some embodiments of the method, the at least one first primer pair (1) comprises at least one forward primer that begins in gene 2, 5' of the fusion site, and optionally includes the fusion site. In some embodiments of the method, the at least one first primer pair (1) comprises at least one reverse primer that begins in gene 1, 3' of the fusion site, and optionally includes the fusion site.

In some embodiments of the method, the composition further comprises at least one primer pair specific for a control sequence, e.g., an internal control. Examples of controls that can be used for the presently disclosed assays include, but are not limited to SDH (succinate dehydrogenase), LDHA (lactate dehydrogenase A), NONO, PGK (phosphoglycerate kinase 1), PPIH, HPRT1, beta-actin, GADPH, ACTB, and 16S rRNA. As explained above, each primer set can be associated with a different label (e.g., dye) that emits a signal distinct from the other labels.

In some embodiments of the method, the composition further comprises a DNA polymerase, and optionally a reverse transcriptase. In some embodiments of the method, the composition further comprises dNTPs and/or buffer amenable to polymerization by the DNA polymerase and reverse transcriptase.

In some embodiments of the method, the sample is isolated nucleic acid, e.g., DNA or RNA. In some embodiments, the sample is RNA, e.g., isolated from blood (serum or plasma), bronchoalveolar lavage, or tissue biopsy. In some embodiments, the method is carried out on biological sample having 100 nM or less of the polynucleotide comprising the fusion gene, e.g., 0.01-100 nM, 0.01-25 nM, 0.01-5 nM, 0.02-0.5 nM, or 0.02-0.1 nM.

In some embodiments, the method is carried out on biological sample from an individual, e.g., an individual diagnosed with cancer, e.g., lung cancer (e.g., non-small cell lung cancer (NSCLC), lung squamous cell carcinoma, lung adenocarcinoma), bladder carcinoma, glioblastoma, head and neck cancer, glioma, thyroid carcinoma, ovarian cancer, leukemia, lymphoma, prostate cancer, pancreatic cancer, renal cancer, or breast cancer.

In some embodiments of the method, the first genetic region (gene 1) is selected from the group consisting of ALK, RET, ROS, NTRK, BRAF, ABL, and FGFR. In some embodiments, the first genetic region is ALK, and the second genetic region (gene 2) is selected from the group consisting of EML4, KIF5B, HIP1, KLC1, and TFG. In some embodiments of the method, the first genetic region is RET, and the second genetic region (gene 2) is selected from the group consisting of KIF5B, CCDC6, NCOA4, and TRIM33.

In some embodiments, the method further comprises recommending a course of treatment if a genetic fusion is discovered. In some embodiments, the course of treatment includes radiation therapy or chemotherapy (e.g., cisplatin, carboplatin, paclitaxel, docetaxel. In some embodiments, the course of treatment includes administration of a drug that specifically targets a gene involved in the genetic fusion. For example, a kinase inhibitor or receptor tyrosine kinase inhibitor can be recommended or administered where one of the genes involved in the gene fusion is a kinase that, as a result of the gene fusion, has a higher expression or activity level than without the fusion. Examples of drugs that can be recommended or administered include imatinib, gefinitib, toceranib, erlotinib, tykerb, sunitinib, nilotinib, sorafenib, bosutinib, neratinib, vatalnib, afatinib, crizotinib, ceretinib, GSK1838705A, TAE-684, CEP-14083, AP26113, and NMS-E628. See, e.g., Grande et at. (2011) *Mol. Cancer Ther.* 10:569 and Rajan & Schrump (Apr. 6, 2015) *Sem. Thoracic Cardiovascular Surgery*. In some embodiments, a gene fusion involving ALK is detected, and the course of treatment includes recommendation or administration of a drug selected from the group consisting of crizotinib, ceretinib, GSK1838705A, TAE-684, CEP-14083, AP26113, and NMS-E628, In some embodiments, a gene fusion involving RET is detected and the course of treatment includes recommendation or administration of a drug selected from the group consisting of sorafenib, vandetanib, motesanib, sunitinib, and XL-184 (see, e.g., Mologni (2011) *Curr. Med. Chem.* 18:162).

Further provided are kits for detecting a genetic fusion as described in more detail herein.

DETAILED DESCRIPTION OF THE INVENTION

I. Introduction

Figure 1:
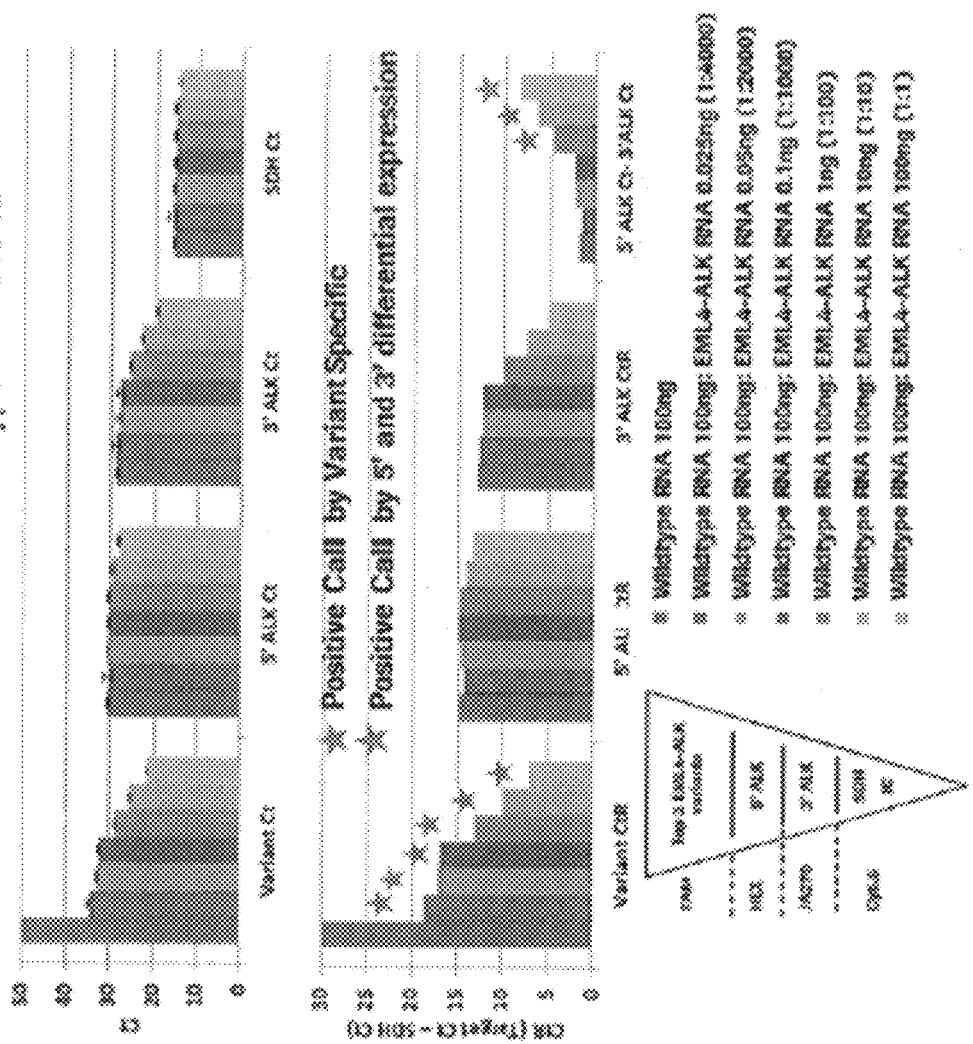
FIG. 1 shows the results from qRT-PCR (quantitative reverse transcriptase PCR) using RNA from wild type cells (control), and wild type RNA spiked with RNA from cells with EML4-ALK fusions at the indicated ratios. The samples in the columns left to right on the graphs are in the same order as listed top to bottom below the graphs. The lop panel shows Ct for each primer set. The primer sets are described in the triangle on the bottom left, along with the respective dyes (FAM, HEX, JA270, and Cy5.5). The bottom panel shows the Relative Ct values (CtR) based on the succinate dehydrogenase internal control (SDH-IC). Note the difference between the 5' of the fusion site amplification and 3' of the fusion site amplification on the right. Stars indicate samples with an EML/4-ALK fusion detected. Each decrease in Ct value correlates to an increase in the amount of template by 2-fold.

The inventors have discovered a novel, quantitative, and multiplex method of detecting fusions between genetic regions. The presently disclosed methods require only a small amount of patient sample that can be gathered non-invasively, e.g., circulating free RNA (cfRNA) from plasma.

Current tests require either biopsy or large amounts of plasma, due to the limited amount of circulating nucleic acids originating from a tumor. The presently described methods allow for an extremely sensitive, one tube assay to detect gene fusions in at least two ways. In the first, multiple primers specific for various fusions are used to amplify across the fusion site. In the second, two sets of primers that amplify outside the fusion site are used. One primer set amplifies a region of the affected gene that is upstream of the fusion site (5' of the fusion site), and the other primer set amplifies a region of the affected gene that is downstream of the fusion site (3' of the fusion site). Finally, a control set of primers specific for a known sequence can be included to ensure the presence and quality of nucleic acid in the sample. The method thus utilizes four sets of primers: (i) fusion site specific, (ii) 5' of the fusion site; (iii) 3' of the fusion site; and optionally (iv) control. Each of (i), (ii), (iii), and (iv) can be associated with a different label or dye, and detected using a 4-channel detector.

The fusion site specific primers (i) include at least one forward (5') and at least one reverse (3') primer, but can include multiple variants of each to capture different fusion site variants. As shown in the Examples herein, seven different forward primers and two different reverse primers were used to detect the fusion site for ALK. Nine different forward primers and two different reverse primers were used to detect the fusion site for RET. The fusion site specific primers (i) can be arranged on either side of, but not including the fusion site, or can be arranged so that one of the primers covers the fusion site. Either the forward or reverse primer, or both, can be labeled so that all of the amplification products from the fusion site specific primers (i) include the same label.

The 5' of the fusion site primers (ii) and 3' of the fusion site primers (iii) can be designed for either member fusion gene, depending on the type of fusion. The goal is to compare the amount of the genetic regions on either side of the fusion site. If they are equal, then no fusion is present. That is, a region 5' of the breakpoint and a region 3' of the breakpoint are still intact. If they are not equal, one side of the gene is expressed at a lower level than the other side, indicating that a fusion has occurred. For example with EML4-ALK, a fusion would be detected if the 5' of the fusion site primers resulted in a lower amplification signal than the 3' of the fusion site primers (see Example 1 and FIG. 1). Again, the forward primer, the reverse primer, or both can be labeled so that all of the amplification products from (ii) include the same label, and all of the amplification products from (iii) include the same label.

The number of primers in the variant specific primer set (i) can be expanded to detect several different variants of a given genetic fusion. The 5' of the fusion site primers (ii) and 3' of the fusion site primers (iii) provide a backup, in case a particular variant fusion is not amplified and detected by the variant specific primer set (i).

The control set of primers (iv) can be specific for any nucleic acid that would be expected to appear in plasma, e.g., a housekeeping gene. Again, either the forward or reverse or both can be labeled so that the amplification products from (iv) include the same label.

II. Definitions

A "genetic fusion" is hybrid chromosomal sequence formed by joining of two chromosomal locations that were previously separate. Fusion can occur between genes on the same chromosome (e.g., interstitial deletion or chromosomal inversion) or on different chromosomes (e.g., translocation).

A "fusion gene" is a hybrid gene formed by the joining of two genes that were previously separate. The fusion gene need not necessarily include coding sequence from both genes, but can include non-coding sequence from one of the genes, e.g., promoter or 3' untranslated regions. The denomination of genes that comprise a fusion gene as "gene 1," "gene 2," "gene A," "gene B," etc., is used to distinguish between genes that make up the fusion and does not necessarily refer to the position of the genes in the fusion.

The terms "fusion site," "fusion point," "breakpoint" and like terms refer to the point in a genetic fusion where a nucleotide from one gene or genetic location is found adjacent to a nucleotide from another gene or genetic location.

The terms "target region," "target portion," "target fragment," and like terms refer to a region of a target nucleic acid sequence that is to be amplified and/or analyzed.

The terms "nucleic acid," "polynucleotide," and "oligonucleotide" refer to polymers of nucleotides (e.g., ribonucleotides or deoxyribo-nucleotides) and includes naturally-occurring (adenosine, guanidine, cytosine, uracil and thymidine), non naturally occurring, and modified nucleic acids. The term is not limited by length (e.g., number of monomers) of the polymer. A nucleic acid maybe single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

The term "primer" refers to a short nucleic acid (an oligonucleotide) that acts as a point of initiation of polynucleotide strand synthesis by a nucleic acid polymerase under suitable conditions. Polynucleotide synthesis and amplification reactions typically include an appropriate buffer, dNTPs and/or rNTPs, and one or more optional cofactors, and are carried out at a suitable temperature. A primer typically includes at least one target-hybridized region that is at least substantially complementary to the target sequence. This region of is typically about 15 to about 40 nucleotides in length. A "primer pair" refers to a forward primer and reverse primer (sometimes called 5' and 3' primers) that are complementary to opposite strands of a target sequence and designed to amplify the target sequence. The forward and reverse primers are arranged within an amplifiable distance of each other on the target sequence, e.g., about 10-5000 nucleotides, or about 25-500 nucleotides. A "primer set" refers to one or more primer pairs, or a combination of at least one forward primer and at least one reverse primer. For example, a primer set can include 3 forward primers and 1 reverse primer, so that 3 distinct amplification products can potentially be produced.

A primer set or primer pair that is specific for a sequence (or portion of a gene) that is 5' (or 3') of a fusion site (or breakpoint) refers to primers used to amplify a sequence that does not include the fusion site or breakpoint.

As used herein, "probe" means any molecule that is capable of selectively binding to a specifically intended target biomolecule, for example, a nucleic acid sequence of interest to be bound, captured or hybridized by the probes.

The words "complementary" or "complementarity" refer to the ability of a nucleic acid in a polynucleotide to form a base pair with another nucleic acid in a second polynucleotide. For example, the sequence A-G-T (A-G-U for RNA) is complementary to the sequence T-C-A (U-C-A for RNA). Complementarity may be partial, in which only some of the nucleic acids match according to base pairing, or complete, where all the nucleic acids match according to base pairing. A probe or primer is considered "specific for" a target sequence if it is at least partially complementary to the target sequence. Depending on the conditions, the degree of complementarity to the target sequence is typically higher for a shorter nucleic acid such as a primer (e.g., greater than 80%, 90%, 95%, or higher) than for a longer sequence.

The terms "identical" or "percent identity," in the context of two or more nucleic acids, or two or more polypeptides, refer to two or more sequences or subsequences that are the same or have a specified percentage of nucleotides, or amino acids, that are the same (e.g., about 60% identity, e.g., at least any of 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." Percent identity is typically determined over optimally aligned sequences, so that the definition applies to sequences that have deletions and/or additions, as well as those that have substitutions. The algorithms commonly used in the art account for gaps and the like. Typically, identity exists over a region comprising an a sequence that is at least about 8-25 amino acids or nucleotides in length, or over a region that is 50-100 amino acids or nucleotides in length, or over the entire length of the reference sequence.

The term "allele" refers to a sequence variant of a gene. One or more genetic differences can constitute an allele.

The term "kit" refers to any manufacture (e.g., a package or a container) including at least one reagent, such as a nucleic acid probe or probe pool or the like, for specifically amplifying, capturing, tagging/converting or detecting RNA or DNA as described herein.

The term "amplification conditions" refers to conditions in a nucleic acid amplification reaction (e.g., PCR amplification) that allow for hybridization and template-dependent extension of the primers. The term "amplicon" refers to a nucleic acid molecule that contains all or a fragment of the target nucleic acid sequence and that is formed as the product of in vitro amplification by any suitable amplification method. Various PCR conditions are described in *PCR Strategies* (Innis et al., 1995, Academic Press, San Diego, Calif.) at Chapter 14: *PCR Protocols: A Guide to Methods and Applications* (Innis et al., Academic Press, NY, 1990)

The terms "thermostable nucleic acid polymerase" or "thermostable polymerase" refers to a polymerase enzyme, which is relatively stable at elevated temperatures when compared, for example, to polymerases from *E. coli*. A thermostable polymerase is suitable for use under temperature cycling conditions typical of the polymerase chain reaction ("PCR"). Exemplary thermostable polymerases include those from *Thermus thermophilus, Thermus caldophilus, Thermus* sp. Z05 (see, e.g., U.S. Pat. No. 5,674,738) and mutants of the *Thermus* sp. Z05 polymerase, *Thermus aquaticus, Thermus flavus, Thermus filiformis, Thermus* sp. sps17, *Deinococcus radiodurans*, Hot Spring family B/clone 7, *Bacillus stearothermophilus, Bacillus caldotenax, Thermotoga maritima, Thermotoga neapolitana* and *Thermosipho africanus*, and modified versions thereof.

The term "sample" or "biological sample" refers to any composition containing or presumed to contain nucleic acid from an individual. The term includes purified or separated components of cells, tissues, or blood, e.g., DNA, RNA, proteins, cell-free portions, or cell lysates. In some embodiments, analysis is conducted on plasma samples isolated from blood; the terms "detected in patient's blood" and "detected in patient's plasma" are used interchangeably to mean that blood is obtained from the patient and plasma derived therefrom is used for the analysis. A sample can also refer to other types of biological samples, e.g., skin, plasma, serum, whole blood and blood components (buffy coat), saliva, urine, tears, seminal fluid, vaginal fluids, tissue biopsies, and other fluids and tissues, including paraffin embedded tissues. Samples also may include constituents and components of in vitro cultures of cells obtained from an individual, including cell lines.

A "control" sample or value refers to a sample that serves as a reference, usually a known reference, for comparison to a test sample or test conditions. For example, a test sample can be taken from a test condition, e.g., from an individual suspected of having cancer, and compared to samples from known conditions, e.g., from a cancer-free individual (negative control), or from an individual known to have cancer (positive control). In the context of the present disclosure, an example of a negative control would be a biological sample from a known healthy (non-cancer) individual, and an example of a positive control would be a biological sample from a patient or cell line known to have a particular gene fusion. A control can also represent an average value or a range gathered from a number of tests or results. A control can also be prepared for reaction conditions. For example, a positive control for the presence of nucleic acid could include primers or probes that will detect a sequence known to be present in the sample, while a negative control would be free of nucleic acids. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The term "diagnosis" refers to a relative probability that a subject has a disorder such as cancer or certain type of cancer (e.g., resulting from a gene fusion). Similarly, the term "prognosis" refers to a relative probability that a certain future outcome may occur in the subject. For example, in the context of the present disclosure, diagnosis can refer to classification of a cancer or the likelihood that an individual will be responsive to a particular therapy. The terms are not intended to be absolute, as will be appreciated by any one of skill in the field of medical diagnostics.

The terms "therapy," "treatment," and "amelioration" refer to any reduction in the severity of symptoms. In the case of treating cancer, treatment can refer to, e.g., reducing tumor size, number of cancer cells, growth rate, metastatic activity, reducing cell death of non-cancer cells, reduced nausea and other chemotherapy or radiotherapy side effects, etc. The terms "treat" and "prevent" are not intended to be absolute terms. Treatment and prevention can refer to any delay in onset, amelioration of symptoms, improvement in patient survival, increase in survival time or rate, etc. Treatment and prevention can be complete (undetectable levels of neoplastic cells) or partial, such that fewer neoplastic cells are found in a patient than would have occurred without the treatment. The effect of treatment can be compared to an individual or pool of individuals not receiving the treatment (e.g., individuals having the same genetic fusion), or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The term "threshold cycle" or "Ct" is a measure of relative concentration and is commonly used in real-time PCR (also referred to as qPCR). Ct refers to the intersection of an amplification curve and a threshold line. The threshold line is often set at a point when signal can be detected above background, or when an amplification reaction enters the exponential phase. Ct can be affected by concentration of target and amplification conditions, e.g., the effect of conditions on detectable labels and amplification efficiency. A higher Ct corresponds to a longer time to reach the threshold, be it due to low target concentration or inefficient amplification.

The terms "individual," "subject," "patient," and like terms are used interchangeably and refer to, except where indicated, mammals such as humans and non-human primates, as well as rabbits, rats, mice, dogs, cats, and other mammalian species. The term does not necessarily indicate that the subject has been diagnosed with a particular disease, but typically refers to an individual under medical supervision. A patient can be seeking treatment, monitoring, adjustment or modification of an existing therapeutic regimen, etc. A patient can include individuals that have not received treatment, are currently receiving treatment, have had surgery, and those that have discontinued treatment.

The terms "label," "tag," "detectable moiety," and like terms refer to a composition detectable by spectroscopic, photochemical, biochemical, immunochemical, chemical, or other physical means. For example, useful labels include fluorescent dyes, luminescent agents, radioisotopes (e.g., $^{32}P$, $^{3}H$), electron-dense reagents, or an affinity-based moiety, e.g., a "His tag" for purification, or a "strepavidin tag" that interacts with biotin.

Unless defined otherwise, technical and scientific terms used herein have the same meaning as commonly understood by a person of ordinary skill in the art. See, e.g., Pfaffl, Methods: The ongoing evolution of qPCR, vol. 50 (2010); van Pelt-Verkuil et al. Principles and Technical Aspects of PCR Amplification, Springer (2010); Lackie, DICTIONARY OF CELL AND MOLECULAR BIOLOGY, Elsevier (4th ec. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

III. Fusion Genes

A number of cancer-associated fusion genes are known, and appear in all manner of cancers. These commonly occur where one member of the fusion is a kinase involved in a pro-growth signaling pathway, and the other member contributes to elevated or constitutive expression or signaling. The presently described compositions and methods can be used to detect any genetic fusion, as primers can be designed to amplify and detect the fusion site, and to amplify and detect regions upstream and downstream of the fusion site. Moreover, because the disclosed methods can be carried out with limited amounts of cfRNA, localization of a tumor and biopsy are not required.

Examples of fusion genes that can be detected according to the present disclosure include those involving tyrosine kinases such as ALK, RET, ROS, NTRK (neurotrophic tyrosine receptor kinase), BRAF, ABL, and FGFR (fibroblast growth factor receptor). Particular examples include but are not limited to EML4-ALK, KIF5B-ALK, HIP1-ALK, KLC1-ALK, TFG-ALK, KIF5B-RET, CCDC6-RET, NCOA4-RET, TRIM33-RET, ERC1-RET, BCR-ABL, FGFR3-TACC3, C11orf95-RELA, DNAJB1-PRKACA, TMPRSS2-ERG, PML-RARA, EGFR-SEPT14, RPS6KB1-VMP1, ETV6-NTRK3, SND1-BRAF, MLL-MLLT10, MLL-ELL, EHMT1-GRIN1, NSD1-ZFN346, PPP1CB-PLB1, KDM2A-RHOD, NSD1-NUP98, and MLL-MLLT4 (see, e.g., Yoshihara et al. (Dec. 15, 2014) Oncogene).

IV. Preparation of Sample

Samples for testing genetic fusions can be obtained from any source, but are advantageously obtained in a non-invasive manner, e.g., from blood or a blood fraction. Samples for the present methods can also be taken from bronchoalveolar lavage or tissue biopsy. Methods for isolating nucleic acids from biological samples are known, e.g., as described in Sambrook, and several kits are commercially available (e.g., High Pure RNA Isolation Kit, High Pure Viral Nucleic Acid Kit, and MagNA Pure LC Total Nucleic Acid Isolation Kit from Roche).

In some embodiments, DNA is prepared, and used as template for the presently disclosed amplification and detection methods. In some embodiments, RNA Is prepared. When RNA is used as template for amplification by PCR, a reverse transcription step is required to prepare cDNA. A DNA polymerase such as Taq or another thermostable polymerase can then be used to effect amplification.

As shown in the Examples, the presently disclosed methods are extraordinarily sensitive, and can be used to detect fusion mutations from as few as 20 copies in a sample diluted 1:4000 in wild type RNA. This allows for detection in samples where the target sequence is very rare, e.g., circulating free RNA (cfRNA).

In some embodiments, the sample is RNA is isolated from blood plasma. Depending on the condition of the patient, about 1-10 mL of plasma can be obtained for testing (usually about 2 mL). Kits for isolating circulating free RNA are commercially available, e.g., from Norgen Biotek Corp or Qiagen.

V. Amplification and Detection

Nucleic acid amplification can be carried out using any primer dependent method. In some embodiments, the amplification is quantitative, so that the relative or actual abundance of a given amplification target can be determined by the amount of amplification product.

DNA-based methods can be used for the presently disclosed amplification and detection methods, e.g., PCR. In some embodiments, real time or quantitative PCR is used (RTPCR or qPCR). qPCR allows for reliable detection and measurement of products generated during each cycle of PCR process. Such techniques are well known in the art, and kits and reagents are commercially available, e.g., from Roche Molecular Systems, Life Technologies, Bio-Rad, etc. See, e.g., Pfaffl (2010) Methods: The ongoing evolution of qPCR vol. 50. In some embodiments, the amplification and detection are carried out in the presence of a dual labeled probe (e.g., a TaqMan, CPT, LNA, or MGB probe) labeled with a quencher and a fluorophore (see, e.g., Gasparic et al. (2010) Anal. Bioanal. Chem. 396:2023).

In some embodiments, a preliminary reverse transcription step is carried out (also referred to as RT-PCR, not to be confused with real time PCR). See, e.g., Hierro et al. (2006) 72:7148. The term "qRT-PCR" as used herein refers to reverse transcription followed by quantitative PCR. Both reactions can be carried out in a single tube without interruption, e.g., to add reagents.

RNA based amplification methods can also be used, e.g., transcription mediated amplification (TMA) or nucleic acid sequence based amplification (NASBA). See, e.g., Fakruddin et al. (2013) J Pharm Bioallied Sci. 5:245; van Deursen et al.(1999) Nucl. Acids Res. 27:e15; Kamisango et al. (1999) J Clin. Microbial 37:310.

A probe, or one or both primers in a primer pair can be labeled with any substance or component that directly or indirectly emits or generates a delectable signal. In some embodiments, the labels are fluorophores (dyes), many of which are reported in the literature and known to those skilled in the art, and many of which are commercially available. Fluorophores are described, e.g., in Cardullo et al. (1988) Proc. Natl. Acad. Sci. USA 85:8790; Hochstrasser et al. (1992) Biophysical Chemistry 45: 133; Selvin (1995) Methods in Enzymology 246: 300; Steinberg, Ann. Rev. Biochem., 40:83-114 (1971); and Wang et al., Anal. Chem. 67: 1197-1203(1995).

The following are examples of fluorophores that can be used as labels: 4-acetamido-4'-isothiocyanatostilbene-2, 2'disulfonic acid; acridine; acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate [0070] N-(4-anilino-1-naphthyl)maleimide; anthranilamide; BODIPY; Brilliant Yellow; coumarin; 7-amino-4-methylcoumarin (AMC, Coumarin 120)/7-amino-4-trifluoromethylcoumarin (Coumaran 151); cyanine dyes; cyanosine 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4' diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansykhloride); 4-(4'-dimethylaminophenylazo)benzoic acid (DABCYL); 4-dimethylaminophenylazophenyl-4'-isothiocyanate (DABITC); eosin; eosin isothiocyanate; erythrosin B; erythrosin isothiocyanate; ethidium; 5-carboxyfluorescein (FAM); 5-(4,6-dichlorotriazin-2-yl)aminofluorescein (DTAF); 2',7'-dimethoxy-4',5'-dichloro-6-carboxyfluorescein (JOE); fluorescein; fluorescein isothiocyanate; fluorescamine; IR144; IR1446; Malachite Green isothiocyanate; 4-methylumbeLiferone; ortho cresolphthalein; nitrotyrosine; pararosaniline; Phenol Red; phycoerythrin (including but not limited to B and R types); o-phthaldialdehyde; pyrene; pyrene butyrate; succinimidyl 1-pyrene butyrate; quantum dots; Reactive Red 4 (Cibacron Brilliant Red 3B-A); 6-carboxy-X-rhodamine (ROX); 6-carboxyrhodamine (R6G); lissamine rhodamine B sulfonyl chloride rhodamine; rhodamine B; rhodamine 123; rhodamine X isothiocyanate; sulforhodamme B; sulforhodamine 101; sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; and lanthanide chelate derivatives.

Any of the listed fluorophores (dyes) can be used in the presently described assays to label a nucleic acid as described herein. Fluorophores can be attached by conventional covalent bonding, using appropriate functional groups on the fluorophore and/or nucleic acid.

As noted above, a dual labeled probe can be used for detection. The dual labeled probe can comprise a fluorophore, such any of the fluorophores listed above, and a quencher. Suitable quenchers include but are not limited to DDQ-I, Dabcyl, Eclipse, Iowa Black FQ, BHQ-1, QSY-7, BHQ-2, DDQ-II. Iowa Black RQ, QSY-21, and BHQ-3. For fluorophores having an emission maximum between 500 and 550 nm (e.g., FAM, TET, and HEX), a quencher with an absorption maxima between 450 and 500 nm can be selected (e.g., dabcyl or BHQ-1). For fluorophores having an emission maximum above 550 nm (e.g., rhodamine and Cy dyes), a quencher with an absorption maxima above 550 nm can be selected (e.g., BHQ-2). See, e.g., Johansson (2003) *Meth. Mol. Biol.* 335:17 for considerations in selecting dye-quencher pairs.

Detection devices are known in the art and can be selected as appropriate for the selected labels. Detection devices appropriate for quantitative PCR include the Cobas® and bight Cycler® systems (Roche), PRISM 7000 and 7300 real-time PCR systems (Applied Biosystems), etc.

VI. Kits

In some embodiments, reagents and materials for carrying out the presently disclosed methods are included in a kit. In some embodiments, the kit includes components for obtaining, storing, and/ or preparing sample. Such components include, e.g., sterile needles and syringes, EDTA-lined tubes, buffers (e.g., for binding nucleic acid to, and elution from a matrix), RNase inhibitors, and/ or DNase, etc.

In some embodiments, the kit includes primers for detecting a genetic fusion, e.g., a gene fusion. In some embodiments, the kit comprises (i) at least one first primer pair specific for the fusion site in the genetic fusion; (ii) a second primer pair specific for a portion of sequence upstream of (5' to) the fusion site; and (iii) a third primer pair specific for a portion of sequence downstream of (3' to) the fusion site. In some embodiments, the kit further comprises a positive control primer pair (e.g., sequence from a housekeeping gene, or another sequence expected to be in the sample) and/or a negative control primer set (e.g., designed to amplify a sequence not expected in the sample to be tested such as sequence from a different organism). The at least one first primer pair (i) can include more than one primer pair that can detect variants of the genetic fusion. In some embodiments, the multiple primer pairs include multiple forward primers that utilize the same reverse primer, or multiple reverse primers that utilize the same forward primer.

In some embodiments, each of the primer sets is packaged in separate tubes, e.g., to be added in ratios to be determined by the user. In some embodiments, one or more or all of the primer sets are packaged in a single tube with predetermined ratios.

The kit can also include enzymes, such as reverse transcriptase and or DNA polymerase. In some embodiments, the DNA polymerase is a thermostable DNA polymerase capable of amplifying in thermocycling conditions, e.g., Taq or a Taq derivative. In some embodiments, the kit includes dNTPs. In some embodiments, the kit includes buffers conducive to polymerization/amplification by the selected polymerases.

In some embodiments, the kit includes controls, e.g., a polynucleotide that is wild type at the genetic fusion to be detected (i.e., no genetic fusion), or a polynucleotide that includes the genetic fusion to be detected.

The kit can also include consumables such as sample tubes or vials; reaction containers (e.g., tubes, multiwell plates, microfluidic chips or chambers, etc), as well as directions for use or reference to a website.

VII. Examples

A. Example 1: Detection of EML4-ALK Fusions in Plasma and Titred Cellular RNA

In this example, we tested a multiplex, quantitative RT-PCR method to detect EML4-ALK fusions. Four different primer sets are used in a single-tube assay to reduce the amount of sample needed to achieve measurable, reliable results.

The primers shown in Table 1 can be used, in addition to a primer pair specific for SDH, labeled with Cy5.5. The first set of forward and reverse primers (SEQ ID NOs:1-62) amplify across various EML4-ALK fusions. Forward and reverse primers can be used in single pairs or in any combination to amplify different fusion products, as will be appreciated by one of skill in the art. The primers specific for a region 5' of the breakpoint on ALK (replaced by EML4 in the fusion) are shown as SEQ ID NOs:63-72 (five each of forward and reverse primer options). The primers specific for a region 3' of the breakpoint (present in both fusion and non-fusion genes) are shown as SEQ ID NOs:73-82 (five each of forward and reverse primer options). The reverse primers in all reactions served as primers for the reverse transcriptase reactions.

TABLE 1

| Probe dye | Forward primer | SEQ ID NO | Sequence |
|---|---|---|---|
| FAM | EML13F1 | 1 | ACACCTGGGAAAGGACCTAAA |
|  | EML13F2 | 2 | CACACCTGGGAAAGGACCTAAA |
|  | EML13F3 | 3 | CCACACCTGGGAAAGGACCTA |
|  | EML13F4 | 4 | CCACACCTGGGAAAGGACCT |
|  | EML13F5 | 5 | CCACACCTGGGAAAGGACC |
|  | EML13F6 | 6 | CCACACCTGGGAAAGGAC |
|  | EML13F7 | 7 | CCCACACCTGGGAAAGGAC |

TABLE 1-continued

| Probe dye | Forward primer | SEQ ID NO | Sequence |
|---|---|---|---|
| | EML13F8 | 8 | GCCCACACCTGGGAAAGGA |
| | EML13F9 | 9 | AGCCCACACCTGGGAAAG |
| | EML13F10 | 10 | GAGCCCACACCTGGGAAA |
| | EML20F1 | 11 | CTCGGGAGACTATGAAATATTGTACT |
| | EML20F2 | 12 | TCGGGAGACTATGAAATATTGTACT |
| | EML20F3 | 13 | CGGGAGACTATGAAATATTGTACT |
| | EML20F4 | 14 | CTCGGGAGACTATGAAATATTGTAC |
| | EML20F5 | 15 | ACTCGGGAGACTATGAAATATTGTA |
| | EML20F6 | 16 | AACTCGGGAGACTATGAAATATTGTA |
| | EML20F7 | 17 | TAACTCGGGAGACTATGAAATATTGTA |
| | EML20F8 | 18 | TAACTCGGGAGACTATGAAATATTGT |
| | EML20F9 | 19 | TAACTCGGGAGACTATGAAATATTGTA |
| | EML20F10 | 20 | ACTCGGGAGACTATGAAATATTGTAC |
| | EML6F1 | 21 | AAGCATAAAGATGTCATCATCAACCAA |
| | EML6F2 | 22 | AGCATAAAGATGTCATCATCAACCAA |
| | EML6F3 | 23 | GCATAAAGATGTCATCATCAACCAA |
| | EML6F4 | 24 | CATAAAGATGTCATCATCAACCAAG |
| | EML6F5 | 25 | GCATAAAGATGTCATCATCAACCAAG |
| | EML6F6 | 26 | GCATAAAGATGTCATCATCAACCA |
| | EML6F7 | 27 | GCATAAAGATGTCATCATCAACC |
| | EML6FB | 28 | AGCATAAAGATGTCATCATCAACC |
| | EML6F9 | 29 | AAGCATAAAGATGTCATCATCAACC |
| | EML6F10 | 30 | AAGCATAAAGATGTCATCATCAAC |
| | EML2AF1 | 31 | CTCAGTGAAAAAATCAGTCTCAAG |
| | EML2AF2 | 32 | CTCAGTGAAAAAATCAGTCTCAAGT |
| | EML2AF3 | 33 | TCAGTGAAAAAATCAGTCTCAAGTA |
| | EML2AF4 | 34 | TCAGTCAAAAAATCAGTCTCAAGTAA |
| | EML2AF5 | 35 | CAGTGAAAAAATCAGTCTCAAGTAAAG |
| | EML18F1 | 36 | CAGCTCTCTGTGATGCGCTA |
| | EML18F2 | 37 | CTCTCTGTGATGCGCTACT |
| | EML18F3 | 38 | TCTCTGTGATGCGCTACTCAA |
| | EML18F4 | 39 | GCTCTCTGTGATGCGCTAC |
| | EML18F5 | 40 | CTGTGATGCGCTACTCAATAG |
| | KIF25F1 | 41 | AGAAGAGGGCATTCTGCACA |
| | KIF25F2 | 42 | GAGGGCATTCTGCACAGA |
| | KIF25F3 | 43 | GAGGGCATTCTGCACAGAT |
| | KIF25F4 | 44 | GAAGAGGGCATTCTGCACAG |
| | KIF25F5 | 45 | GGGCATTCTGCACAGATTG |
| | KIF17F1 | 46 | GAACTAGTCCAGCTTCGAGCA |
| | KIF17F2 | 47 | TGAAGAACTAGTCCAGCTTCGA |
| | KIF17F3 | 48 | CTAGTCCAGCTTCGAGCACAA |
| | KIF17F4 | 49 | AAGAACTAGTCCAGCTTCGAG |
| | K1F17F5 | 50 | GTCCAGCTTCGAGCACAAG |
| | EMLMAF5 | 51 | TCTGTGGGATCATGATCTGAATC |
| | Reverse primer | | |
| | ALK20R1 | 52 | GCTCTGCAGCTCCATCTG |
| | ALK20R2 | 53 | GGCTCTGCAGCTCCATCT |
| | ALK20R3 | 54 | GGGCTCTGCAGCTCCATC |
| | ALK20R4 | 55 | GGGCTCTGCAGCTCCAT |
| | AIK20R5 | 56 | GGGCTCTGCAGCTCCA |
| | ALK20R6 | 57 | TGCAGCTCCATCTGCATGG |
| | ALK20R7 | 58 | GCAGCTCCATCTGCATGG |
| | ALK20R8 | 59 | CAGCTCCATCTGCATGGC |
| | AIK20R9 | 60 | AGCTCCATCTGCATGGC |
| | ALK20R10 | 61 | GCTCCATCTGCATGGCT |
| | A20REVC4 | 62 | CGGAGCTTGCTCAGCTTGTA |
| HEX | Forward primer | | |
| | ALKex4F1 | 63 | GAGATCCTCCTGATGCCCA |
| | ALKex4F2 | 64 | GTCCTGATGCCCACTCCA |
| | ALKex4F3 | 65 | TGATGCCCACTCCAGGGAA |
| | ALKex4F4 | 66 | TCCTCCTGATGCCCACTC |
| | ALKex4F5 | 67 | GATCCTCCTGATGCCCAC |
| | Reverse primer | | |
| | ALKex5R1 | 68 | TTGTCTGGACGCCCGATT |
| | ALKex5R2 | 69 | GACGCCCGATTCTTCCCT |
| | ALKex5R3 | 70 | TCTGGACGCCCGATTCTT |
| | ALKex5R4 | 71 | TGTCTGGACGCCCGATTC |
| | ALKex5R5 | 72 | CTGGACGCCCGATTCTTC |
| JA270 | Forward primer | | |
| | ALKex24F1 | 73 | GCCTGTGGCTGTCAGTATT |
| | ALKex24F2 | 74 | CTGTGGCTGTCAGTATTTGGA |
| | ALKex24F3 | 75 | CTGTCAGTATTTGGAGGAAAACCA |
| | ALKex24F4 | 76 | CCTGTGGCTGTCAGTATTTG |
| | ALKex24F5 | 77 | TGTGGCTGTCAGTATTTGGAG |

TABLE 1-continued

| Probe dye | Forward primer | SEQ ID NO | Sequence |
|---|---|---|---|
| | Reverse primer | | |
| | ALKex25R1 | 78 | CCTGACAGCTCAAGAGGCA |
| | ALKex25R2 | 79 | TGACAGGTCAAGAGGCAGTT |
| | ALKex25R3 | 80 | AGGTCAAGAGGCAGTTTCT |
| | ALKex25R4 | 81 | CTGACAGGTCAAGAGGCAG |
| | ALKex25R5 | 82 | GGTCAAGAGGCAGTTTCTG |

The reaction conditions were as follows. For each reaction, 25 uL of input RNA was added to a RT-PCR reaction mix comprising forward and reverse primers, labeled probe, buffer, dUTP, dTTP, dATP, dGTP, UNG, RT, and Z05 enzyme to a final volume of 50 uL.

The primer combinations in Table 2 were used to generate the representative results shown in FIG. 1.

TABLE 2

| Probe dye | Forward primer | Reverse primer |
|---|---|---|
| FAM | EML13F1 | ALK20R1 |
| | EML20F2 | |
| | EML6F3 | |
| | EML2AF2 | |
| | KIF17F2 | |
| | KIF25F4 | |
| | EML14AF5 | A20REVC4 |
| HEX (5') | ALKex4F1 | ALKex5R3 |
| JA270 (3') | ALKex24F2 | ALKex25R3 |

Reactions were run in a cobas® LC480 with four fillers used for the multiplex reactions: FAM, HEX, JA270, and CY5.5 (internal control).

We have tested this method using RNA from EML4-ALK positive cell lines NCI-H460 (HTB-177), NCI-H2228, and EML4-ALK Fusion Variant 1 cell line from Horizon Discovery, as well as from NSCLC formalin fixed paraffin embedded tissue (FFPET) and plasma specimens.

In the case of plasma, we extracted cfRNA using the Qiagen ExoRNA Easy Kit. Because the yield of cfRNA is too low to be measured accurately, we input a fixed volume (¼ of total) of the extracted plasma cfRNA into the qRT-PCR.

In the multiplex qRT-PCR, one channel (FAM in this case) detects amplification of variant specific ALK fusions, while a second channel (HEX) detects the amplification of the region 5' of the breakpoint, and a third channel (JA270) detects amplification of the region 3' of the breakpoint. A fourth channel (Cy5.5) is used for the standardizing control, which assures that the cfRNA input was sufficient in quantity and quality.

Representative results are shown in FIG. 1. The wild type RNA was obtained from NCI-1975 (CRL-5908) cell line and the EML4-ALK RNA was obtained from the EML4-ALK Fusion Variant 1 cell line. EML-ALK RNA was titrated into wild type RNA as indicated to determine the limit of detection.

Both the fusion variant specific primer set (e.g., SEQ ID NOs:1-62), and the primers designed to differentially measure the regions 5' and 3' of the fusion point resulted in detection of fusion gene amplification products. The fusion variant specific primers detected 25 pg of EML4-ALK fusion positive RNA blended at a 1:4000 dilution with wild type RNA. The 5' and 3' differential measure was able to detect 1 ng EML4-ALK RNA blended at a 1:100 dilution with wild type RNA.

These results are impressive because the multiplex assay is sensitive enough to detect 20 copies of fusion RNA species in the variant specific reaction. The reactions to differentially measure the regions 5' and 3' of the fusion point can generate a positive signal from a blended sample with only 1% of the RNA containing the fusion. The multiplex assay is also extraordinarily specific, as no positive signal wax observed with up to 200 ng wild type RNA. Given that cfRNA from a tumor is generally rare compared to wild type cfRNA, these results are encouraging even for early diagnosis.

B. Example 2: Detection of CCDC6-RET Fusions in Plasma and Titred Cellular RNA

In this example, we tested the multiplex qRT-PCR for its ability to detect CCDC6-RET fusions in RNA from cell lines, as well as from plasma.

The primers shown in Table 3 can be used to detect CCDC6-RET fusions, in addition to a primer pair specific for SDH, labeled with Cy5.5.

Representative forward primers (SEQ ID NOs:83-160) and reverse primers (SEQ ID NOs:161-198) amplify across various CCDC6-RET fusions. Representative primers specific for a region 5' of the breakpoint on RET (replaced by CCDC6 in the fusion) are shown as SEQ ID NOs:199 and 200. Representative primers specific for a region 3' of the breakpoint (present in both fusion and non-fusion genes) are shown as SEQ ID NOs:201 and 202. Again, forward and reverse primers can be used in single pairs or in any combination to amplify different fusion products, as will be appreciated by one of skill in the art. The reverse primers in all reactions served as primers for the reverse transcriptase reactions.

TABLE 3

| Probe dye | Forward primer | SEQ ID NO | Sequence |
|---|---|---|---|
| FAM | KIF15F1 | 83 | GAATTGCTGTGGGAAATAATGATG |
| | KIF15F2 | 84 | GAATTGCTGTGGGAAATAATGAT |
| | KIF15F3 | 85 | ATTGCTGTGGGAAATAATGATGTAAAG |
| | KIF15F4 | 86 | TTGCTGTGGGAAATAATGATGTAAAG |
| | KIF15F5 | 87 | TGCTGTGGGAAATAATGATGTAAAG |
| | KIF15F6 | 88 | GCTGTGGGAAATAATGATGTAAAG |
| | KIF15F7 | 89 | GAATTGCTGTGGGAAATAATGATGTAAA |
| | KIF15F8 | 90 | GAATTGCTGTGGGAAATAATGATGTAA |

TABLE 3-continued

| | | |
|---|---|---|
| KIF15F9 | 91 | AATTGCTGTGGGAAATAATGATGTAAA |
| KIF15F10 | 92 | ATTGCTGTGGGAAATAATGATGTAAA |
| KIF15F11 | 93 | ATTGCTGTGGGAAATAATGATGTAA |
| KIF15F12 | 94 | AATTGCTGTGGGAAATAATGATGTA |
| KIF15F13 | 95 | ATTGCTGTGGGAAATAATGATGTA |
| KIF15F14 | 96 | GAATTGCTGTGGGAAATAATGATGTA |
| KIF15F15 | 97 | GAATTGCTGTGGGAAATAATGATGT |
| KIF16F1 | 98 | CATGTCAGCTTCGTATCTCTCAA |
| KIF16F2 | 99 | ATGTCAGCTTCGTATCTCTCAA |
| KIF16F3 | 100 | CATGTCAGCTTCGTATCTCTCA |
| KIF16F4 | 101 | GCATGTCAGCTTCGTATCTCTC |
| KIF16F5 | 102 | CATGTCAGCTTCGTATCTCTC |
| KIF16F6 | 103 | GCATGTCAGCTTCGTATCTCT |
| KIF16F7 | 104 | GCATGTCAGCTTCGTATCTC |
| KIF16F8 | 105 | CAGCATGTCAGCTTCGTATC |
| KIF16F9 | 106 | TAGCAGCATGTCAGCTTCGTA |
| KIF16F10 | 107 | AGCAGCTATGTCAGCTTCG |
| KIF22F1 | 108 | AGGACCTGGCTACAAGAGTTAA |
| KIF22F2 | 109 | GGACCTGGCTACAAGAGTTAA |
| KIF22F3 | 110 | GGACCTGGCTACAAGAGTTAAA |
| KIF22F4 | 111 | AGGACCTGGCTACAAGAGTTAAA |
| KIF22F5 | 112 | AGGACCTGGCTACAAGAGTTA |
| KIF22F6 | 113 | GGACCTGGCTACAAGAGTTA |
| KIF22F7 | 114 | GACCTGGCTACAAGAGTTAAAAG |
| KIF22F8 | 115 | ACCrGGCTACAAGAGTTAAAAG |
| KIF22F9 | 116 | AGGACCTGGCTACAAGAGTT |
| KIF22F10 | 117 | GGACCTGGCTACAAGAGTT |
| KIF23F1 | 118 | TTGAACAGCTCACTAAAGTGCACAAA |
| KIF23F2 | 119 | TGAACAGCTCACTAAAGTGCACAAA |
| KIF23F3 | 120 | GAACAGCTCACTAAAGTGCACAAA |
| KIF23F4 | 121 | AACAGCTCACTAAAGTGCACAAA |
| KIF23F5 | 122 | ACAGCTCACTAAAGTGCACAAA |
| KIF23F6 | 123 | GAACAGCTCACTAAAGTGCACAA |
| KIF23F7 | 124 | AACAGCTCACTAAAGTGCACAA |
| KIF23F8 | 125 | ACAGCTCACTAAAGTGCACAA |
| KIF23F9 | 126 | TGAACAGCTCACTAAAGTGCACA |
| KIF23F10 | 127 | AACAGCTCACTAAAGTGCACA |
| CCDC1F1 | 128 | TGCGCAAAGCCAGCGT |
| CCDC1F2 | 129 | CGACCTGCGCAAAGCCA |
| CCDC1F3 | 130 | GACCTGCGCAAAGCCAG |
| CCDC1F4 | 131 | CCTGCGCAAAGCCAGC |
| CCDC1F5 | 132 | ACCTGCGCAAAGCCAGC |
| CCDC1F6 | 133 | CTGCGCAAAGCCAGCGT |
| CCDC1F7 | 134 | GACCTGCGCAAAGCCAGC |
| CCDC1F8 | 135 | CGACCTGCGCAAAGCC |
| NCO6F1 | 136 | TGTATCTCCATGCCAGAGCAG |
| NCO6F2 | 137 | GTATCTCCATGCCAGAGCAG |
| NCO6F3 | 138 | CTGTATCTCCATGCCAGAGCA |
| NCO6F4 | 139 | GCTGTATCTCCATGCCAGAG |
| NCO6F5 | 140 | GGCTGTATCTCCATGCCAGA |
| NCO6F6 | 141 | GGCTGTATCTCCATGCCAG |
| NCO6F7 | 142 | AGGCTGTATCTCCATGCCA |
| NCO6F8 | 143 | GAGGCTGTATCTCCATGCCA |
| NCO6F9 | 144 | AGAGGCTGTATCTCCATGC |
| NCO6F10 | 145 | GAGAGGCTGTATCTCCATGC |
| TRIM14F1 | 146 | CAGGAGGAGTGCTTGCATG |
| TRIM14F2 | 147 | AGGAGGAGTGCTTGCATG |
| TRIM14F3 | 148 | CAGGAGGAGTGCTTGCAT |
| TRIM14F4 | 149 | CAGGAGGAGTGCTTGCA |
| TRIM14F5 | 150 | GCAGGAGGAGTGCTTGC |
| TRIM14F6 | 151 | GGCAGGAGGAGTGCTTG |
| TRIM14F7 | 152 | TGGCAGGAGGAGTGCTT |
| TRIM14F8 | 153 | ATGGCAGGAGGAGTGCT |
| TRIM14F9 | 154 | GATGGCAGGAGGAGTGC |
| TRIM14F10 | 155 | GAGGATGGCAGGAGGAGT |
| TRIM11F1 | 156 | GCTGCCAGATATTCCACCCAT |
| TRIM11F2 | 157 | GCTGCCAGATATTCCACCCATA |
| TRIM11F3 | 158 | CTGCCAGATATTCCACCCATACA |
| TRIM11F4 | 159 | CATCGCTGCCAGATATTCCAC |
| TRIM11F5 | 160 | CTGCCAGATATTCCACCCATAC |
| Reverse primer | | |
| RET12R1 | 161 | AGAGTTTTTCCAAGAACCAAGTTGT |
| RET12R2 | 162 | CTAGAGTTTTTCCAAGAACGAAGTTGT |
| RET12R3 | 163 | GTAGAGTTTTTCCAAGAACCAAGTTC |
| RKT12R4 | 164 | CTAGAGTTTTTCCAAGAACCAAGTT |
| RET12R5 | 165 | CTAGAGTTTTTCCAAGAACCAAGT |
| RET12R6 | 166 | CTAGAGTTTTTCCAAGAACCAAG |
| RET12R7 | 167 | TAGAGTTTTTCCAAGAACCAAGTTCTT |
| RET12R8 | 168 | GAGTTTTTCCAAGAACCAACTTCTT |

TABLE 3-continued

| | | | |
|---|---|---|---|
| | RET12R9 | 169 | AGTTTTTCCAAGAACCAAGTTCTT |
| | RET12R10 | 170 | GTTTTTCCAAGAACCAAGTTCTT |
| | RET12R11 | 171 | TAGAGTTTTTCCAAGAACCAAGTTCT |
| | RET12R12 | 172 | TAGAGTTTTTCCAAGAACCAAGTTC |
| | RET12R13 | 173 | AGAGTTTTTCCAAGAACCAAGTTC |
| | RET12R14 | 171 | AGAGTTTTTCCAAGAACCAAGTT |
| | RET12R15 | 175 | AGAGTTTTTCCAAGAACCAAGT |
| | RET12R16 | 176 | CTCGTAGAGTTTTTCCAAGAACCAA |
| | RET12R17 | 177 | CTCCTAGAGTTTTTCCAAGAACCA |
| | RET12R18 | 178 | TCCTAGAGTTTTTCCAAGAACCAA |
| | RET12R19 | 179 | CCTAGAGTTTTTCCAAGAACCAA |
| | RET12R20 | 180 | GAGTTTTTCCAAGAACCAAGTTCT |
| | RET8R1 | 181 | GTCTCTTGCTGACTGCACAGG |
| | RET8R2 | 182 | TCTCTTGCTGACTGCACAGG |
| | RET8R3 | 183 | CTCTTGCTGACTGCACAGG |
| | RET8R4 | 184 | TCTCTTGCTGACTGCACAG |
| | RET8R5 | 185 | GTCTCTTGCTGACTGCACAG |
| | RET8R6 | 18G | CGTCTCTTGCTGACTGCACA |
| | RET8R7 | 187 | CCGTCTCTTGCTGACTGCA |
| | RET8R8 | 188 | GCCGTCTCTTGCTGACTG |
| | RET8R9 | 189 | AGCCGTCTCTTGCTGACT |
| | RET11DR1 | 190 | CTCCGGAAGGTCATCTCAGCT |
| | RET11DR2 | 191 | TCCGGAAGGTCATCTCAGCT |
| | RET11DR3 | 192 | CCGGAAGGTCATCTCAGCT |
| | RET11DR4 | 193 | TCCGGAAGGTCATGTCAGC |
| | RET11DR5 | 194 | CTCCGGAAGGTCATCTCAG |
| | RET11DR6 | 195 | CCTCCGGAAGGTCATCTCA |
| | RET11DR7 | 196 | GCCTCCGGAAGGTCATCTC |
| | RET11DR8 | 197 | GGCCTCCGGAAGGTCATC |
| | RET11DR9 | 198 | GGGCCTCCGGAAGGTCA |

| Probe dye | Forward primer | | |
|---|---|---|---|
| Hex (5') | RETex5F1 | 199 | TTCGTGCGGGCGACCGTA |
| | Reverse primer | | |
| | RETex6R1 | 200 | GGTGCGGTTCTCCGAGAT |

| Probe dye | Forward primer | | |
|---|---|---|---|
| JA270 (3') | RETex17F1 | 201 | CCGGATGGAGAGGCCAGA |
| | Reverse primer | | |
| | RETex18R1 | 202 | TTTTGTCCGGCTCCTGCT |

Figure 2:
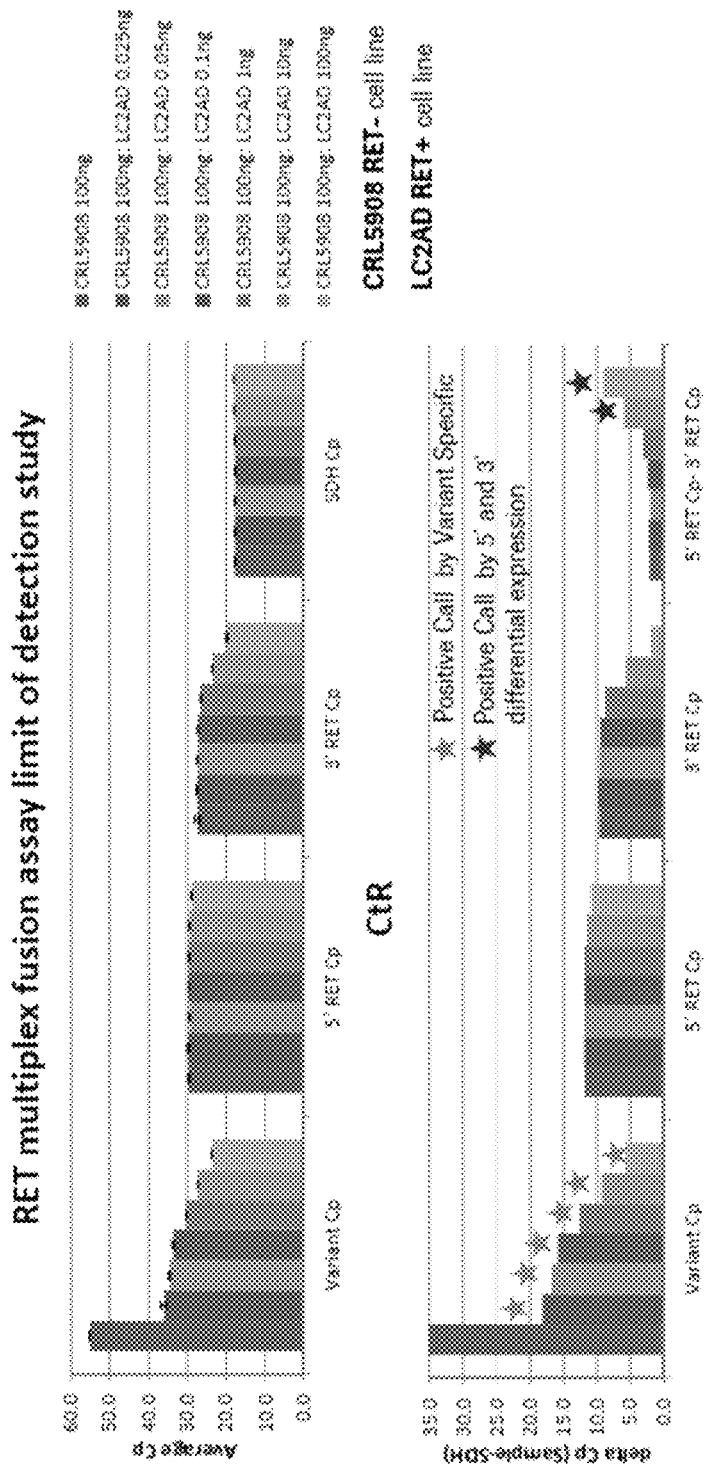
FIG. 2 shows the results from qRT-PCR to detect CCDC6-RET. The top panel shows the Ct values for wild type RNA (CRL5908), or wild-type spiked with the indicated amount of RNA from cells carrying the CCDC6-RET (LC2AD). The bottom panel shows CtR values, and the difference between the 5' of the fusion site amplification and 3' of the fusion site amplification on the right. Again, the samples in the columns left to right on the graphs are in the same order as listed top to bottom beside the graphs.
Figure 3:
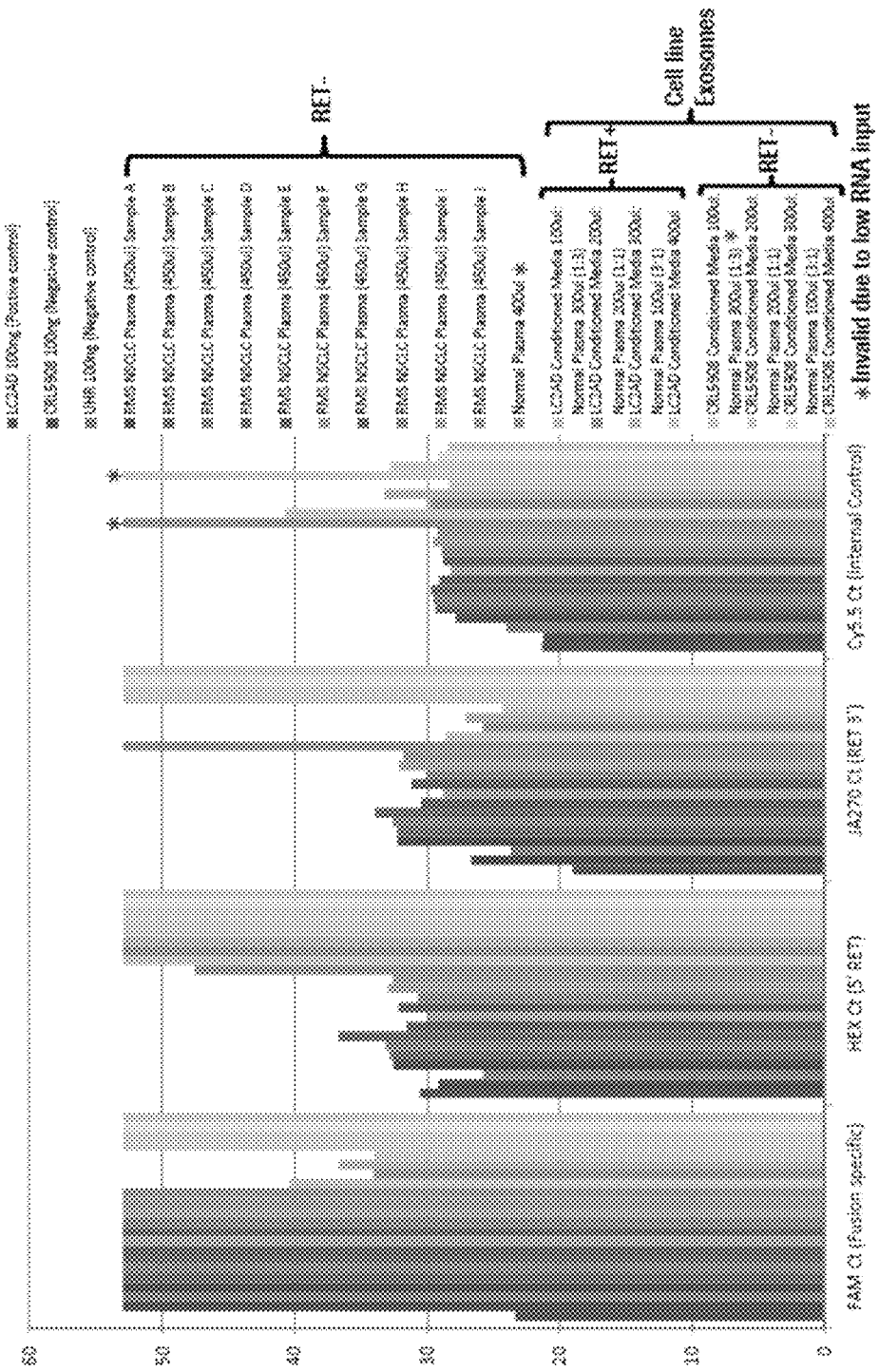
FIG. 3 shows the Ct values for the indicated primer sets (same as in FIG. 2). The samples in the columns left to right on the graph are in the same order as listed top to bottom beside the graph. In this case, the samples include RNA from cfRNA, as well as RNA from CCDC6-RET positive cells titrated into wild type RNA.
Figure 4:
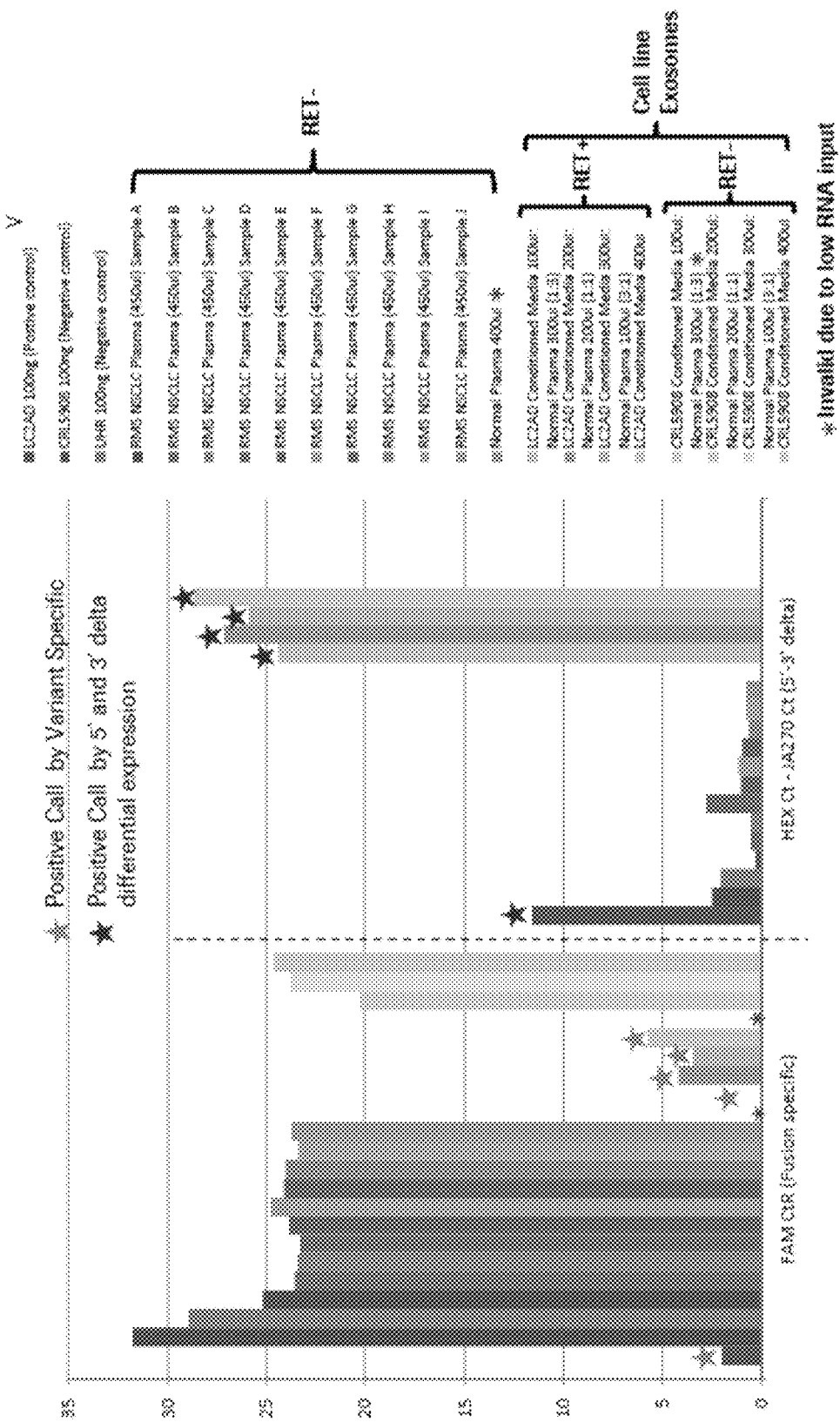
FIG. 4 shows CtR values from the data shown in FIG. 3. Again, the difference between the 5' of the fusion site amplification and 3' of the fusion site amplification is shown on the right. Stars indicate detection of a CCDC6-RET fusion.

The reaction conditions were the same as those described in Example 1, end the primer combinations in Table 4 were used to generate the representative results shown in FIGS. 2-4.

TABLE 4

| Probe dye | Forward primer | Reverse primer |
|---|---|---|
| FAM | KIF15F8 | RET12R17 |
| | KIF16F2 | |
| | KIF22F1 | |
| | KIF23F9 | |
| | CCDC1F6 | |
| | NCO6F5 | |
| | TRIM14F8 | |
| | TRIM11F2 | RET11DR9 |
| HEX | RETex5F1 | RETex6R1 |
| JA270 | RETex17F1 | RETex18R1 |

We tested this method using RNA from the CCDC6-RET positive cell line LC-2AD, wild type cell line CRL-5908, and "universal human RNA" (UHR), a mixture of RNA from various tissues. We also tested RNA from NSCLC FFPET specimens, and normal and NSCLC plasma.

The results are shown in FIGS. 2-4. FIG. 2 shows that, similar to the results for EML4-ALK, the CCDC6-RET fusion could be detected with extraordinary sensitivity. The variant specific amplification could detect as little as 25 pg fusion positive RNA mixed with 100 ng wild type RNA, while the 5' and 3' differential measure was able to detect the fusion with as little as 10 ng RNA.

FIG. 3 shows the Ct values for reactions using plasma. The RMS NSCLC Plasma samples were tested and shown to be negative for CCDC6-RET fusions. Normal plasma was also mixed with RNA from fusion positive (LC2AD) or wild type (CRL-5908) cells. The control-corrected data is shown in FIG. 4. Only those samples with RNA from the fusion positive cell line showed a positive result.

Again, the results are encouraging because of the unexpected sensitivity and specificity. No fusion was detected even in plasma samples from NSCLC patients.

While the invention has been described in detail with reference to specific examples, it will be apparent to one skilled in the art that various modifications can be made within the scope of this invention. Thus the scope of the invention should not be limited by the examples described herein. All patents, publications, websites, Genbank (or other database) entries disclosed herein are incorporated by reference in their entireties.

We claim:

1. A method for detecting if a biological sample from an individual carries a fusion gene, said method comprising:
   (A) carrying out a reverse transcription reaction and an amplification reaction with the biological sample from the individual and a composition comprising: (i) at least one first primer pair that is specific for a fusion site between gene 1 and gene 2, wherein the at least one primer pair comprises at least one forward primer beginning on the 5' side of the fusion site and at least one reverse primer beginning on the 3' side of the fusion site; (ii) a second primer pair specific for a portion of gene 1 that is 5' of the fusion site; and (iii) a third primer pair specific for a portion of gene 1 that is 3' of the fusion site;
   (B) determining the amount of amplification product from the at least one first primer pair;
   (C) detecting the presence or absence of a difference in the amount of amplification product from the second primer pair and the amount of amplification product from the third primer pair;
   (D) detecting a fusion gene if:
   (i) the amount of amplification product from the at least one first primer pair determined in step (B) is greater than the amount of amplification product from the at least one first primer pair and a control polynucleotide that does not carry the fusion gene; or
   (ii) the presence of a difference is detected in step (C).

2. The method of claim 1, wherein the biological sample includes RNA.

3. The method of claim 2, wherein the biological sample includes RNA from plasma of the individual.

4. The method of claim 1, wherein gene 1 is selected from ALK, RET, RQS, NTRK, BRAF, ABL, and FGFR.

5. The method of claim 4, wherein gene 1 is ALK, and gene 2 is selected from the group consisting of EML4, KIF5B, HIP1, KLC1, and TFG.

6. The method of claim 4, wherein gene 1 is RET, and gene 2 is selected from the group consisting of KIF5B, CCDC6, NCOA4, and TRIM33.

7. The method of claim 1, wherein the reverse transcription and amplification reactions are carried out using quantitative reverse transcription polymerase chain reaction (qRT-PCR).

* * * * *

SEQUENCE LISTING

<160> NUMBER OF SEQ ID NOS: 202

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acacctggga aaggacctaa a                                              21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cacacctggg aaaggaccta aa                                             22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccacacctgg gaaaggacct a                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccacacctgg gaaaggacct                                                20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccacacctgg gaaaggacc                                                 19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
ccacacctgg gaaaggac                                                     18

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cccacacctg ggaaaggac                                                    19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcccacacct gggaaagga                                                    19

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agcccacacc tgggaaag                                                     18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagcccacac ctgggaaa                                                     18

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcgggagac tatgaaatat tgtact                                            26

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```
tcgggagact atgaaatatt gtact     25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgggagacta tgaaatattg tact     24

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcgggagac tatgaaatat tgtac     25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
actcgggaga ctatgaaata ttgta     25

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aactcgggag actatgaaat attgta     26

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
taactcggga gactatgaaa tattgta     27

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
taactcggga gactatgaaa tattgt     26

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
taactcggga gactatgaaa tattgta                                      27

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
actcgggaga ctatgaaata ttgtac                                       26

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aagcataaag atgtcatcat caaccaa                                      27

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agcataaaga tgtcatcatc aaccaa                                       26

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcataaagat gtcatcatca accaa                                        25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cataaagatg tcatcatcaa ccaag                                        25

```
<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcataaagat gtcatcatca accaag                                         26

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gcataaagat gtcatcatca acca                                           24

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcataaagat gtcatcatca acc                                            23

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agcataaaga tgtcatcatc aacc                                           24

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aagcataaag atgtcatcat caacc                                          25

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aagcataaag atgtcatcat caac                                           24
```

```
<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctcagtgaaa aaatcagtct caag                                          24

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctcagtgaaa aaatcagtct caagt                                         25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcagtgaaaa aatcagtctc aagta                                         25

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcagtgaaaa aatcagtctc aagtaa                                        26

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cagtgaaaaa atcagtctca agtaaag                                       27

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cagctctctg tgatgcgcta                                               20

<210> SEQ ID NO 37
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ctctctgtga tgcgctact                                                    19

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tctctgtgat gcgctactca a                                                 21

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gctctctgtg atgcgctac                                                    19

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctgtgatgcg ctactcaata g                                                 21

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
agaagagggc attctgcaca                                                   20

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gagggcattc tgcacaga                                                     18

<210> SEQ ID NO 43
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gagggcattc tgcacagat                                                   19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gaagagggca ttctgcacag                                                  20

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gggcattctg cacagattg                                                   19

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gaactagtcc agcttcgagc a                                                21

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgaagaacta gtccagcttc ga                                               22

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctagtccagc ttcgagcaca a                                                21

<210> SEQ ID NO 49
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 49
aagaactagt ccagcttcga g                                            21

<210> SEQ ID NO 50
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtccagcttc gagcacaag                                               19

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tctgtgggat catgatctga atc                                          23

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gctctgcagc tccatctg                                                18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggctctgcag ctccatct                                                18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gggctctgca gctccatc                                                18

<210> SEQ ID NO 55
<211> LENGTH: 17
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 55
gggctctgca gctccat                                                      17

<210> SEQ ID NO 56
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gggctctgca gctcca                                                       16

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tgcagctcca tctgcatgg                                                    19

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcagctccat ctgcatgg                                                     18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cagctccatc tgcatggc                                                     18

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
agctccatct gcatggc                                                      17

<210> SEQ ID NO 61
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 61
gctccatctg catggct                                                    17

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cggagcttgc tcagcttgta                                                 20

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gagatcctcc tgatgccca                                                  19

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ctcctgatgc ccactcca                                                   18

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tgatgcccac tccagggaa                                                  19

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tcctcctgat gcccactc                                                   18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 67
gatcctcctg atgcccac                                                 18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ttgtctggac gcccgatt                                                 18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gacgcccgat tcttccct                                                 18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tctggacgcc cgattctt                                                 18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tgtctggacg cccgattc                                                 18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ctggacgccc gattcttc                                                 18

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gcctgtggct gtcagtatt                                               19

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ctgtggctgt cagtatttgg a                                            21

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ctgtcagtat ttggaggaaa acca                                         24

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cctgtggctg tcagtatttg                                              20

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tgtggctgtc agtatttgga g                                            21

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cctgacaggt caagaggca                                               19

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 79
tgacaggtca agaggcagtt                                              20

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
aggtcaagag gcagtttct                                               19

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctgacaggtc aagaggcag                                               19

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggtcaagagg cagtttctg                                               19

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gaattgctgt gggaaataat gatg                                         24

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gaattgctgt gggaaataat gat                                          23

<210> SEQ ID NO 85
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
```
attgctgtgg gaataatga tgtaaag          27

<210> SEQ ID NO 86
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ttgctgtggg aataatgat gtaaag           26

<210> SEQ ID NO 87
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
tgctgtggga aataatgatg taaag           25

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gctgtgggaa ataatgatgt aaag            24

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gaattgctgt gggaaataat gatgtaaa        28

<210> SEQ ID NO 90
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gaattgctgt gggaaataat gatgtaa         27

<210> SEQ ID NO 91
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
aattgctgtg ggaaataatg atgtaaa          27

<210> SEQ ID NO 92
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
attgctgtgg gaaataatga tgtaaa           26

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
attgctgtgg gaaataatga tgtaa            25

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aattgctgtg ggaaataatg atgta            25

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
attgctgtgg gaaataatga tgta             24

<210> SEQ ID NO 96
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gaattgctgt gggaaataat gatgta           26

<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gaattgctgt gggaaataat gatgt            25

```
<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
catgtcagct tcgtatctct caa                                              23

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
atgtcagctt cgtatctctc aa                                               22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
catgtcagct tcgtatctct ca                                               22

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gcatgtcagc ttcgtatctc tc                                               22

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
catgtcagct tcgtatctct c                                                21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gcatgtcagc ttcgtatctc t                                                21
```

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
gcatgtcagc ttcgtatctc                                          20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
cagcatgtca gcttcgtatc                                          20

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
tagcagcatg tcagcttcgt a                                        21

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
agcagcatgt cagcttcg                                            18

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
aggacctggc tacaagagtt aa                                       22

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
ggacctggct acaagagtta a                                        21

```
<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
ggacctggct acaagagtta aa                                              22

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
aggacctggc tacaagagtt aaa                                             23

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
aggacctggc tacaagagtt a                                               21

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ggacctggct acaagagtta                                                 20

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gacctggcta caagagttaa aaag                                            24

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
acctggctac aagagttaaa aag                                             23

<210> SEQ ID NO 116
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
aggacctggc tacaagagtt                                              20

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ggacctggct acaagagtt                                               19

<210> SEQ ID NO 118
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
ttgaacagct cactaaagtg cacaaa                                       26

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tgaacagctc actaaagtgc acaaa                                        25

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gaacagctca ctaaagtgca caaa                                         24

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
aacagctcac taaagtgcac aaa                                          23

<210> SEQ ID NO 122
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
acagctcact aaagtgcaca aa                                              22

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gaacagctca ctaaagtgca caa                                             23

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
aacagctcac taaagtgcac aa                                              22

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
acagctcact aaagtgcaca a                                               21

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gaacagctca ctaaagtgca ca                                              22

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
aacagctcac taaagtgcac a                                               21

<210> SEQ ID NO 128
<211> LENGTH: 16
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 128
tgcgcaaagc cagcgt                                                    16

<210> SEQ ID NO 129
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
cgacctgcgc aaagcca                                                   17

<210> SEQ ID NO 130
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gacctgcgca aagccag                                                   17

<210> SEQ ID NO 131
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
cctgcgcaaa gccagc                                                    16

<210> SEQ ID NO 132
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
acctgcgcaa agccagc                                                   17

<210> SEQ ID NO 133
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ctgcgcaaag ccagcgt                                                   17

<210> SEQ ID NO 134
<211> LENGTH: 18
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 134
gacctgcgca aagccagc                                                18

<210> SEQ ID NO 135
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
cgacctgcgc aaagcc                                                  16

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tgtatctcca tgccagagca g                                            21

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gtatctccat gccagagcag                                              20

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ctgtatctcc atgccagagc a                                            21

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gctgtatctc catgccagag                                              20

<210> SEQ ID NO 140
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 140
ggctgtatct ccatgccaga                                                 20

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ggctgtatct ccatgccag                                                  19

<210> SEQ ID NO 142
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
aggctgtatc tccatgcca                                                  19

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gaggctgtat ctccatgcca                                                 20

<210> SEQ ID NO 144
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
agaggctgta tctccatgc                                                  19

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gagaggctgt atctccatgc                                                 20

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 146
caggaggagt gcttgcatg                                        19

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
aggaggagtg cttgcatg                                         18

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
caggaggagt gcttgcat                                         18

<210> SEQ ID NO 149
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
caggaggagt gcttgca                                          17

<210> SEQ ID NO 150
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gcaggaggag tgcttgc                                          17

<210> SEQ ID NO 151
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ggcaggagga gtgcttg                                          17

<210> SEQ ID NO 152
<211> LENGTH: 17
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 152
tggcaggagg agtgctt                                                   17

<210> SEQ ID NO 153
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
atggcaggag gagtgct                                                   17

<210> SEQ ID NO 154
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gatggcagga ggagtgc                                                   17

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gaggatggca ggaggagt                                                  18

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gctgccagat attccaccca t                                              21

<210> SEQ ID NO 157
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
gctgccagat attccaccca ta                                             22

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 158
ctgccagata ttccacccat aca                                           23

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
catcgctgcc agatattcca c                                             21

<210> SEQ ID NO 160
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
ctgccagata ttccacccat ac                                            22

<210> SEQ ID NO 161
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
agagtttttc caagaaccaa gttct                                         25

<210> SEQ ID NO 162
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
ctagagtttt tccaagaacc aagttct                                       27

<210> SEQ ID NO 163
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ctagagtttt tccaagaacc aagttc                                        26

<210> SEQ ID NO 164
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
```
ctagagtttt tccaagaacc aagtt                                                25

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
ctagagtttt tccaagaacc aagt                                                 24

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ctagagtttt tccaagaacc aag                                                  23

<210> SEQ ID NO 167
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
tagagttttt ccaagaacca agttctt                                              27

<210> SEQ ID NO 168
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168 gagttttctcc aagaaccaag ttctt                                               25

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
agttttccca agaaccaagt tctt                                                 24

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170

```
gtttttccaa gaaccaagtt ctt                                          23

<210> SEQ ID NO 171
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
tagagttttt ccaagaacca agttct                                       26

<210> SEQ ID NO 172
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
tagagttttt ccaagaacca agttc                                        25

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173 agagttttc caagaaccaa gttc                                          24

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174 agagttttc caagaaccaa gtt                                           23

<210> SEQ ID NO 175
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175 agagttttc caagaaccaa gt                                            22

<210> SEQ ID NO 176
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
ctcctagagt ttttccaaga accaa                                        25
```

```
<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ctcctagagt ttttccaaga acca                                           24

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
tcctagagtt tttccaagaa ccaa                                           24

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
cctagagttt ttccaagaac caa                                            23

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gagtttttcc aagaaccaag ttct                                           24

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gtctcttgct gactgcacag g                                              21

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
tctcttgctg actgcacagg                                                20
```

```
<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ctcttgctga ctgcacagg                                                19

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
tctcttgctg actgcacag                                                19

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
gtctcttgct gactgcacag                                               20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
cgtctcttgc tgactgcaca                                               20

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ccgtctcttg ctgactgca                                                19

<210> SEQ ID NO 188
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gccgtctctt gctgactg                                                 18
```

```
<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
agccgtctct tgctgact                                                    18

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ctccggaagg tcatctcagc t                                                21

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
tccggaaggt catctcagct                                                  20

<210> SEQ ID NO 192
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
ccggaaggtc atctcagct                                                   19

<210> SEQ ID NO 193
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tccggaaggt catctcagc                                                   19

<210> SEQ ID NO 194
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
ctccggaagg tcatctcag                                                   19

<210> SEQ ID NO 195
```

<210> SEQ ID NO 195
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 195
cctccggaag gtcatctca                    19

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 196
gcctccggaa ggtcatctc                    19

<210> SEQ ID NO 197
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 197
ggcctccgga aggtcatc                     18

<210> SEQ ID NO 198
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
gggcctccgg aaggtca                      17

<210> SEQ ID NO 199
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 199
ttcgtgcggg cgaccgta                     18

<210> SEQ ID NO 200
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 200
ggtgcggttc tccgagat                     18

<210> SEQ ID NO 201
<211> LENGTH: 18

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ccggatggag aggccaga                                                 18

<210> SEQ ID NO 202
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ttttgtccgg ctcctgct                                                 18
```